US006441846B1

(12) United States Patent
Carlbom et al.

(10) Patent No.: US 6,441,846 B1
(45) Date of Patent: Aug. 27, 2002

(54) METHOD AND APPARATUS FOR DERIVING NOVEL SPORTS STATISTICS FROM REAL TIME TRACKING OF SPORTING EVENTS

(75) Inventors: Ingrid B. Carlbom, Summit; Yves D. Jean, Scotch Plains; Sarma V G K Pingali, Basking Ridge, all of NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/100,948

(22) Filed: Jun. 22, 1998

(51) Int. Cl.$^7$ .................................................. H04N 7/18

(52) U.S. Cl. ........................ 348/169; 348/157; 348/159; 700/91; 702/166

(58) Field of Search ................................. 348/169, 157, 348/159; 700/91; 702/166; H04N 7/18

(56) References Cited

U.S. PATENT DOCUMENTS

| | | | | |
|---|---|---|---|---|
| 5,513,854 A | * | 5/1996 | Daver .......................... | 700/91 |
| 5,764,283 A | * | 6/1998 | Pingali et al. .............. | 348/169 |
| 5,912,700 A | * | 6/1999 | Honey et al. ................ | 348/157 |
| 6,100,925 A | * | 8/2000 | Rosser et al. ................ | 348/169 |
| 6,133,946 A | * | 10/2000 | Cavallaro et al. ........... | 348/157 |

OTHER PUBLICATIONS

"Tracking and Counting Moving People", M. Rossi and A. Bozzoli, IEEE 1994, pp. 212–216.
"Human Motion Analysis: A Review", J.K. Aggarwal and Q. Cai, IEEE 1997 ;;. 90–102.
"Asset–2: Real–Time Motion Segmentation and Shape Tracking", S.M. Smith and J.M. Brady, IEEE Transactions on Pattern Analysis and Machine Intelligence, vol. 17, No. 8, Aug. 1995, pp. 814–820.

"Towards Model–Based Recognition of Human Movements in Image Sequences", K. Rohr, CVGIP: Image Understanding, vol. 59, No. 1, Jan., pp. 94–115, 1994.
"Model–based vision: a program to see a walking person", David Hogg, School of Engineering and Applied Sciences, University of Sussex, Brighton, Sussex, UK.
"Towards 3–D model–based tracking and recognition of human movement: a multi–view approach", D.M. Gavrila and L.S. Davis, International Workshop on Automatic Face– and Gesture–Recognition, Zurich 1995, pp. 272–277.

(List continued on next page.)

Primary Examiner—Howard Britton
(74) Attorney, Agent, or Firm—Gary D. Yacura (57) ABSTRACT

A method and apparatus for deriving performance statistics from real time tracking of a sporting event. The method according to the present invention includes a step of obtaining a spatio-temporal trajectory corresponding to the motion of an athlete and based on real time tracking of the athlete. The trajectory is then broken down so that performance information corresponding to the motion of the athlete (such as speed, distance covered, acceleration, etc.) can be derived with respect to time. The information so obtained can be stored in a database or the like for later retrieval or can be used to graphically supplement a video broadcast of a sporting event. The apparatus includes a device for obtaining the trajectory, a computational device for obtaining the performance information based on the obtained trajectory, and a statistical device for compiling the performance information. In particular, the spatio-temporal trajectory may be obtained by an operation on a video image of the sporting event, in which motion regions in the image are identified, and feature points on the regions are tracked as they move, thereby defining feature paths. The feature paths, in turn, are associated in clusters, which clusters generally correspond to the motion of some portion of the athlete (e.g., arms, legs, etc.). The collective plurality of clusters corresponds with the motion of the athlete as a whole.

19 Claims, 9 Drawing Sheets

OTHER PUBLICATIONS

"Towards a System for the Interpretation of Moving Light Displays", Richard F. Rashid, IEEE Transactions on Pattern Analysis and Machine Intelligence, vol. PAMI–2, No. 6, Nov. 1980, pp. 574–581.

"Multiple Object Tracking System with Three Level Continuous Processes", Kazuhiro Fukui et al., IEEE 1992, ;;. 19–27.

"Image Sequence Analysis of Real World Human Motion", Koichiro Akita, Pattern Recognition vol. 17, No. 1, pp. 73–83, 1984.

Model–Based Image Analysis of Human Motion Using Constraint Propagation, Joseph O'Rourke and Normal I. Badler, IEEE Transactions on Pattern Analysis and Machine Intelligence, vol. PAMI–2, No. 6, Nov. 1980, pp. 522–536.

"Global color constancy: recognition of objects by use of illumination–invariant properties of color distributions", Glenn Healey and David Slater, J. Opt. Soc. Am. A., vol. 11, No. 11/Nov. 1994, pp. 3003–3010.

"Finding Trajectories of Feature Points in a Monocular Image Sequence", Ishwar K. Sethi and Ramesh Jain, IEEE Transactions on Pattern Analysis and Machine Intelligence, vol. PAMI–9, No. 1, Jan. 1987, pp. 56–73.

* cited by examiner

METHOD AND APPARATUS FOR DERIVING NOVEL SPORTS STATISTICS FROM REAL TIME TRACKING OF SPORTING EVENTS

BACKGROUND OF THE INVENTION

1. Field of the Invention

The present invention relates to a method and apparatus for tracking moving objects in real time whereby trajectories corresponding to the movement of the objects are determined. More particularly, the present invention relates to a method and apparatus for tracking moving objects, such as athletes, in connection with sporting events and exploiting such tracking to derive information corresponding to the movement of the objects being tracked.

2. Description of Related Art

Tracking systems for moving objects typically generate trajectories corresponding to the motion of an object within the view of a camera. The trajectories or tracks typically consist of a sequence of x, y (location) coordinates and time coordinates. The information from these trajectories has a variety of applications. For example, the information can be used to count the number of objects, such as a people or vehicles, crossing a reference line and to associate a particular direction with each crossing. In addition, such trajectories may be used to determine the number of people present within the field of view of a camera at any instant, which information is useful, for example, for product marketing such as determining the effectiveness of a particular advertisement or advertising technique in a store. Tracking systems may also be employed for measuring consumer traffic throughout, for example, the aisles of a store, etc., including the length of time that particular persons spend in specific aisles.

One field in which real time tracking would be particularly desirable, but is not currently greatly utilized, is in the field of sports.

For example, most sports activities are measured in terms of statistics which highlight various aspects of the sport, such as personal performance (number of points scored, fastest time, etc.), comparative performance (e.g., number of points scored versus opponent), and playing strategy (e.g., number of perimeter baskets scored in a basketball game versus number of inside baskets scored).

Conventionally, most such statistics can be readily measured (e.g., number of points scored, time for running a race, number of errors committed). However, other statistics are of interest, but are relatively difficult to obtain readily, and are certainly difficult to obtain in connection with real time tracking of an event. Such statistics may include distance traveled by a player per an interval of time (e.g., a game, set, quarter, etc.), instantaneous and average player speed and acceleration, shot selection (e.g., in hockey or basketball), or areas of a playing field (court, rink, etc.) covered by a player.

Generally, real time tracking of athletes in a sporting event is challenging, especially because it is difficult to obtain a clean segmentation of an athlete from the background in view of changing lighting conditions, variations in clothing worn by athletes (especially with regard to color), differences in the visual characteristics (for example, reflectivity) of playing surfaces (grass, clay, hardwood, ice, etc.), and the fast and dynamic movement of athletes. Another factor complicating tracking is the simple presence of other moving objects or moving people, in addition to the athlete being tracked.

Several methods or systems have been developed for the tracking of moving objects, including people. However, these conventional systems do not yield a single motion region or even a consistent set of motion regions, which deficiencies are exacerbated when tracking athletes in the midst of highly dynamic movement.

For example, in Rashid, R. F., "Towards A System For The Interpretation Of Moving Light Displays", 2 IEEE Transactions on Pattern Analysis and Machine Intelligence, 574–581 (1980), a method is described for interpreting moving light displays (MLD). In general, Rashid teaches segmenting out from MLD images individual points corresponding to moving people. The individual points are grouped together to form clusters based on, inter alia, the positions and velocities of the individual points; the formed clusters represented individual objects. Tracking is performed by matching points between consecutive frames based on the relative distances between the location of points in the current frame and the location of predicted points in a previous frame. The predicted position is based on the average velocity of the point in the previous frame and the relative distance, which is calculated using a Euclidean function.

The technique described by Rashid has several drawbacks. Specifically, the MLD system requires several frames before a good object separation is obtained, and no criteria is provided for determining when satisfactory object separation has occurred. In addition, no mechanism is provided for propagating the generated clusters to prior and subsequent frames for continuity in the motion representation. This undermines real time operation.

In another tracking system described in Rossi, M. and Bozzoli, A., "Tracking And Counting Moving People", Proceedings Of The Second IEEE International Conference On Image Processing, 212–16(1994), a vertically mounted camera is employed for tracking and counting moving people. This system operates under the assumption that people enter a scene along either the top or bottom of the image where altering zones are positioned for detecting people moving into the scene. In reality, however, people can also appear in a scene, inter alia, from behind another object or from behind an already-identified person. In other words, people may be wholly or partially occluded upon initially entering a scene and would not be identified by this system. The problem of identifying occluded persons is also present in the system described in Rohr, K., "Towards Model Based Recognition Of Human Movements In Image Sequences", 59 Computer Vision, Graphics And Image Processing: Image Understanding, 94–115(1994). Such problems are clearly pertinent to real time tracking of athletes during a sporting event.

In addition, the systems described in Smith, S. M., and Brady, J. M., "A Scene Segmenter: Visual Tracking of Moving Vehicles", 7 Engineering Applications Of Artificial Intelligence 191–204(1994); and "ASSET-2: Real-Time Motion Segmentation And Shape Tracking", 17 IEEE Transactions On Pattern Analysis And Machine Intelligence, 814–20 (1995), are designed specifically for tracking objects such as moving vehicles, and accordingly identify features representing corners or abrupt changes on the boundaries of the vehicles. This approach is based on that tracking objects which are rigid with unchanging contours, and, thus, permits the use of constant velocity or constant acceleration models, techniques clearly unavailable for tracking of people, particularly when tracking people in motion, particularly the dynamic motion of sports where hands and feet may all move with different speeds and in different directions.

In the related U.S. Pat. No. 5,764,283, an apparatus and method are disclosed for tracking moving objects in real time. In particular, an apparatus and method are disclosed in which local features, such as extrema of curvature on boundary contours, are tracked, and trajectories of motion are derived by dynamically clustering the paths of motion of the local features.

SUMMARY OF THE INVENTION

The present invention provides, most generally, a method and apparatus for tracking moving objects, particularly athletes engaged in sporting activities. More particularly, the invention provides an apparatus and method for obtaining information corresponding to the athlete(s) and/or sporting activity being tracked. In one embodiment of the present invention, such information is performance statistics for an athlete derived from real time tracking of that athlete. In another embodiment, such information is an occupancy map, which may be visually manifested, corresponding to the frequency with which an athlete occupies particular regions of a playing field, or the time spent in particular regions of the playing field. In yet another embodiment of the present invention, such information is embodied in a computer-generated replay of the sporting event (or some part thereof) using computer generated characters moving in accordance with motion data collected from real time tracking of the sporting event. In particular, the present invention is intended to be especially useful for enhancing television coverage of sporting events.

The method according to the present invention, in pertinent part, includes the steps of matching and merging a select feature path (representing the motion of the one of usually a plurality of local features of an athlete) with a candidate cluster of feature paths chosen from a plurality of preexisting clusters representing motion of the athlete or object. The select feature path has a portion concurrent or overlapping in time with some of the clusters in the plurality of clusters. The candidate cluster is preferably chosen as the cluster closest in distance to the select path. Once the candidate cluster is chosen and the select feature path merged therewith, the parameters of the candidate cluster are updated based on the parameters of the select path.

The distance between the select path and the preexisting clusters is calculated in accordance with a function having two components. The first component is representative of a maximum displacement between the select feature path and the candidate cluster, and the second component is representative of the difference between velocity vectors defining motion of the select feature path and velocity vectors defining motion of the candidate cluster.

Finally, the method includes steps of using the clusters extrapolated in order to provide real time information about the athlete or the sporting event being tracked. For example, a trajectory of an athlete derived according a cluster of feature paths extrapolated in accordance with the foregoing may be mapped onto a video image in order to provide a visual illustration of the athlete's path of movement. From this, for example, an occupancy map may be generated illustrating the frequency or time spent by the athlete in certain portions of a playing field. Also, the trajectory of the athlete can be analyzed with respect to time in order to provide performance information such as instantaneous and average speed and acceleration and the like. In another example, the trajectory of the athlete can be used to generate computer-driven replays of an athletic event, whereby activity on the playing field is duplicated based on player trajectories derived from real time video tracking.

An apparatus constructed in accordance with the present invention particularly includes a device for calculating the distance between a select feature path representing motion of the features of an object and a plurality of preexisting clusters, some of which overlap in time with the select feature path. The distance is calculated using a function having a first component and a second component. The first component is representative of a maximum displacement between the select feature path and each preexisting cluster, and the second component is representative of the difference between velocity vectors defining motion of the select feature path and velocity vectors defining motion of each preexisting cluster. Another device is also provided for selecting, from the preexisting clusters, a candidate cluster having the smallest distance to the select feature path. In a preferred embodiment, the functions of the distance calculating device and selecting device are both embodied in a computer.

Also, in a preferred embodiment, the apparatus includes a device for obtaining information corresponding to the athlete(s) or sporting event being tracked, such as performance statistics for respective athletes, and a device for compiling and storing the performance statistics. The device for calculating performance statistics may be also embodied in the same computer carrying out the functions of the distance calculating device and the selecting device discussed above.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

The present invention will now be described in detail with reference to the drawings appended hereto, in which.

DETAILED DESCRIPTION OF THE PRESENTLY PREFERRED EMBODIMENTS

The present invention will now be described in detail firstly with respect to an example embodiment in which information obtained from real time tracking of athletes engaged in a sporting event is used to derive performance statistics corresponding to the athletes being so tracked. Thereafter, other embodiments within the contemplated scope of the present invention will also be discussed.

Figure 7:
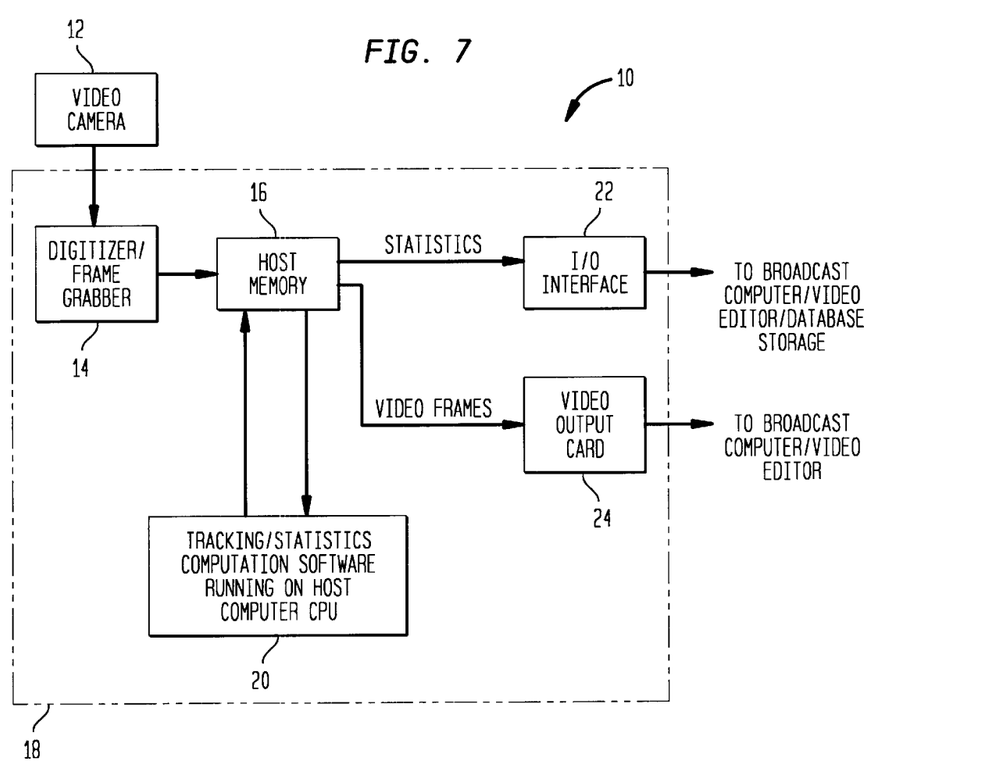
FIG. 7 is a schematic illustration of an example configuration of the apparatus according to the present invention.

A schematic illustration of an apparatus 10 for tracking athletes in real time in accordance with the present invention is depicted in FIG. 7. As there shown, a camera 12 inputs an image in the form of a continuous video signal formed of a serial plurality of previous frames and a current frame to a digitizer/frame grabber 14.

Figure 1:
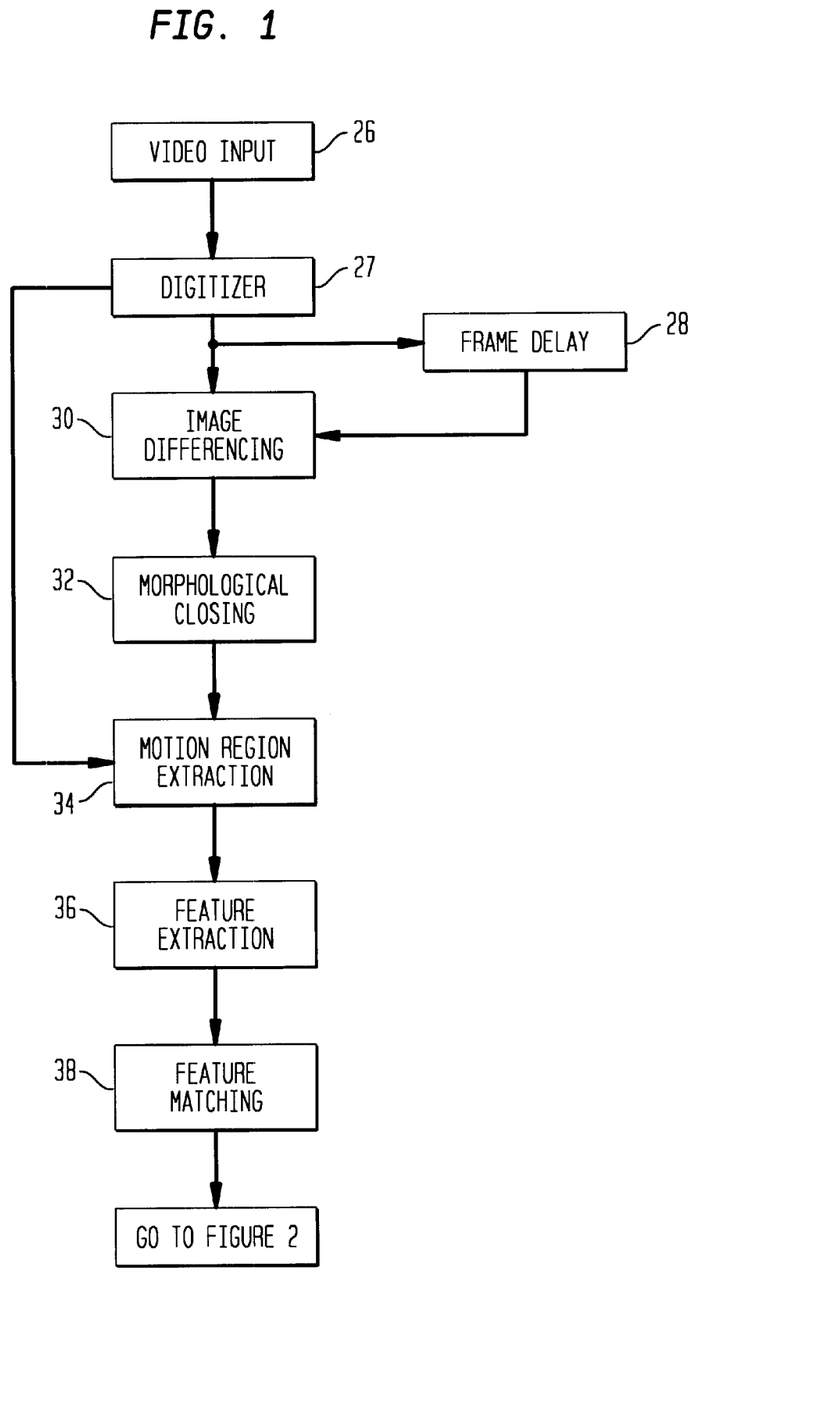
FIG. 1 is a flow chart of a portion of the tracking method according to the present invention, particularly applied to the tracking of athletes participating in a sporting event.

The digitizer/frame grabber 14 digitizes the output from camera 12 and captures a current frame and a previous frame, using a delay 28 (see, for example, FIG. 1).

It will be readily obvious that if the output of camera 12 is already in digital format, then merely a frame grabber need be provided, instead of a digitizer/frame grabber 14.

The captured frames are then transferred to a host memory 16 of a host computer 18. Host computer 18 comprises a CPU 20 for running software to operate on the stored digitized video frames and perform the calculations associated with the derivation of trajectories and with the calculation and compilation of performance statistics derived from the trajectories, as discussed in detail hereinbelow.

The calculated statistics are output via an I/O interface 22 to, for example, a broadcast system for inclusion in a video broadcast of the sporting event, or into a statistical database for later retrieval.

The host computer 18 also includes a video card 24 from which the video frames stored in host memory 16 are output, after having, for example, player trajectories or a player field coverage map mapped thereon so as to be visible to the broadcast viewer.

It should be readily undrstood that with the exception of camera 12, the individual components of apparatus 10 may be implemented by a combination of hardware and/or software elements and the use of either or both is intended to fall within the scope of the present invention.

It is also contemplated that the apparatus according to the present invention may instead comprise, for example, separate pieces of hardware, such as an object identifier for distinguishing an object to be tracked from a static background; an image processor for an image of the so-distinguished object, identifying a contour of the object, and determining feature points on the contour; a feature point comparator for comparing feature points of a current frame with those of a preceding frame; a path identifier for associating corresponding feature points to determine a feature path and for grouping related feature paths into clusters;

and a cluster comparator for merging, as appropriate, a given cluster with a previously existing cluster (see, for example, application No. 08/586,012).

In a working example of the apparatus according to the present invention, a Sony Corporation camcorder (Model No. UVW100B) equipped with a Canon Co. VCL 713 BX zoom lens is used. The camcorder outputs video in conventional RGB format, and is connected to an Octane workstation from Silicon Graphics. The Octane workstation runs the IRIX operating system (version 6.3) and is equipped with two MIPS R10000 processors. The Octane workstation is also equipped with an Octane video card for video input and output. Specifically, the Octane card accepts two simultaneous inputs and two simultaneous outputs, all at 30 fps and in CCIR601 serial digital format. The RGB video output of the camcorder is analog, and is converted into. CCIR601 serial digital format using an Ensemble Designs Serial Box II. The statistics computed by the apparatus are output to a broadcast computer by, for example, an Ethernet connection or an RS232 serial interface, either of which is usable with the Octane workstation. The output video signal from the Octane workstation may, if desirable, be converted to an analog format by a digital to analog converter, such as an Ensemble Designs Serial Box I.

In another working configuration of the apparatus according to the present invention (not illustrated here), the host system is PC based. For example, a PC computer including a 300 Mhz Pentium II processor is also being used, running the Windows NT operating system. A Mutech MV1000 video card with a MV1300 RGB daughter card is used to handle the video input/output in keeping with the foregoing.

Figure 2:
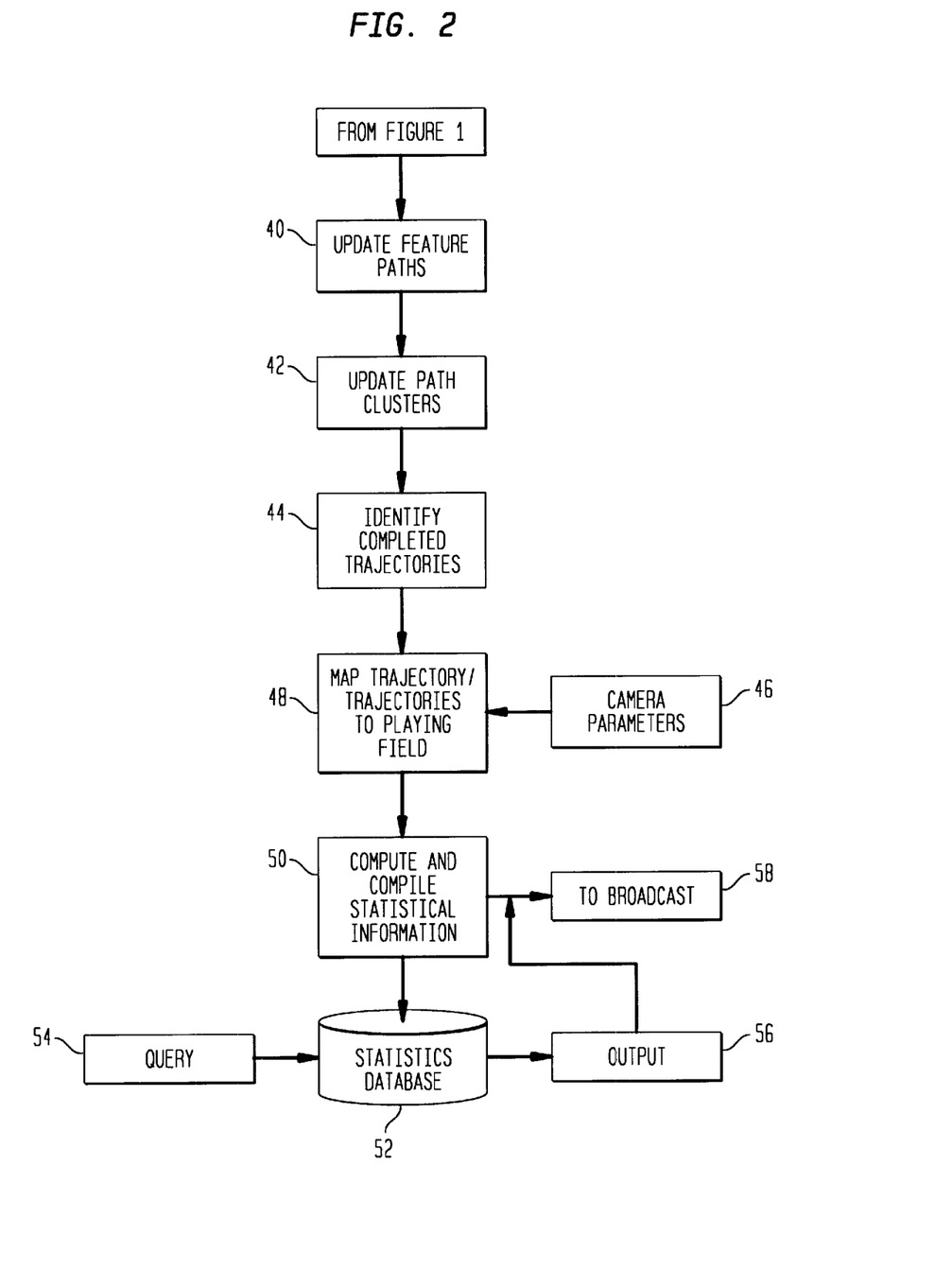
FIG. 2 is a flow chart continuation of the tracking method in FIG. 1, as applied to one embodiment of the present invention by way of example.

With reference now to FIGS. 1 and 2, a preferred method for real time determination of performance statistics related to sporting events will now be described. FIG. 1 is an overall descriptive view of the inventive method according to the present invention.

As shown in FIG. 1, a video input 26 is digitized at step 27 and separated by a frame delay 28 to obtain a previous frame. Thereafter, a current frame and the previous frame are differentiated and thresholded in step 30 in order to identify foreground regions of interest, specifically, foreground regions of motion. Differencing and thresholding in this manner is particularly desirable as it is a fast operation which works across a variety of lighting conditions. As discussed above relative to FIG. 7, if the video input 26 is already in digital format, then the provision of digitizer 27 can be omitted.

In identifying regions of motion in this manner, small gaps sometimes occur in the regions. These gaps can be closed, if desirable, by performing a morphological closing operation 32, as is conventional (see, for example, Giardina et al., "Morphological Methods in Image and Signal Processing," Prentice-Hall, 1988). The differencing and thresholding steps in step 30 and the morphological closing operation in step 32 (if performed) may be represented as:

$$B_t = (H_T(I_t - I_{t-1}) \oplus g) \ominus g \qquad (1)$$

where $B_t$ is a binary image consisting of the regions of interest at time t, $H_t$ is a thresholding operation, $I_t$ is the input image at time t, $I_{t-1}$ is the previous input image at time t-1, and $\oplus$, $\ominus$ represent morphological dilation and erosion operations, respectively, using a structuring element g. The dilation operation essentially uses the element 9 as a filling element that is "wiped" across a motion region to fill in gaps or discontinuities therein left from the differencing operation. This dilation operation actually fills in a space beyond the actual contour of the motion region in order to ensure complete filling (hence, "dilation"). The erosion operation, as implied, uses the structuring element g again, but this time removes the "excess" filled portion past the contour of the motion region so as to leave a completely filled motion region having its original boundary or contour.

The result of the morphological closing step 32 is a binary image of the motion region(s) of interest. The binary image is simply digital data, and must be reassociated with an actual visual image. Therefore, as can be seen in FIG. 1, the digitized video from step 27 is coupled in a conventional manner in step 34 with the binary image of the motion regions so that a video image of the motion regions results.

In step 36, local feature points on the resultant image are identified. One example of feature points that can be used are the extrema of curvature on the contours of the motion regions. As a practical matter when tracking people in motion, such as athletes, the extrema of curvature typically correspond to the extremities of a person, such as the head, arms, and legs.

In step 38, the feature points identified in a current frame are compared with those of the preceding frame to associate most, if not all, of the corresponding feature points in the current and previous frames, as is discussed below. If a feature point in the current frame does not have a corresponding feature point in the previous frame, then the unmatched feature point in the current frame is added in an appropriate location to the contour of the appropriate motion region.

After corresponding pairs of feature points have been identified in step 38, an existing feature path is associated with the corresponding current and prior feature point pairs (step 40), if possible, and the existing feature paths are then grouped into clusters (step 42) representing the motion of the image from which the current feature points were obtained. Like the feature points and feature paths, the clusters have defining parameters indicating, inter alia, spatio-temporal coordinates as well as the number of paths contributing to that particular cluster.

If a particular path is not yet assigned to an existing cluster, the method according to the present invention includes a technique (discussed in detail below) for determining which of the existing clusters is best suited for being associated with that path, whereupon that path is included in that cluster. Once included, the cluster parameters are updated in accordance with the parameters from the newly-included feature path (step 42).

In step 44, the existing clusters are compared with each other to see if any clusters can be merged. In addition, the existing clusters are checked to determine when the last update for each cluster occurred. If the last update occurred outside of a specified time interval, that cluster is examined for validity and, if invalid, is destroyed. The remaining valid clusters (defining trajectories) are then available for use in a variety of applications like extrapolation of performance statistics.

For example, the trajectories identified in step 44 may be mapped back onto the image plane (step 48) (for example, onto the image plane of a playing field) using video camera calibration parameters 46 (such as orientation and position of the camera relative to the playing field) so as to be visible as part of the video image, for example, superimposed over a playing field so as to illustrate a player's path of travel.

The mathematical representations of the clusters may be operated on by a computing device or by software running on a computer so as to derive performance statistics therefrom (step 50). The statistics may be stored in a database 52, whereby queries 54 thereto result in search results 56 being identified. Alternatively, the statistics may be fed to the video broadcast 58 where they can be shown as captioning or the like, in a known manner, in real time. Database search results 56 may also be fed to the broadcast 58, for example, in response to a query from a television announcer.

Figure 3:
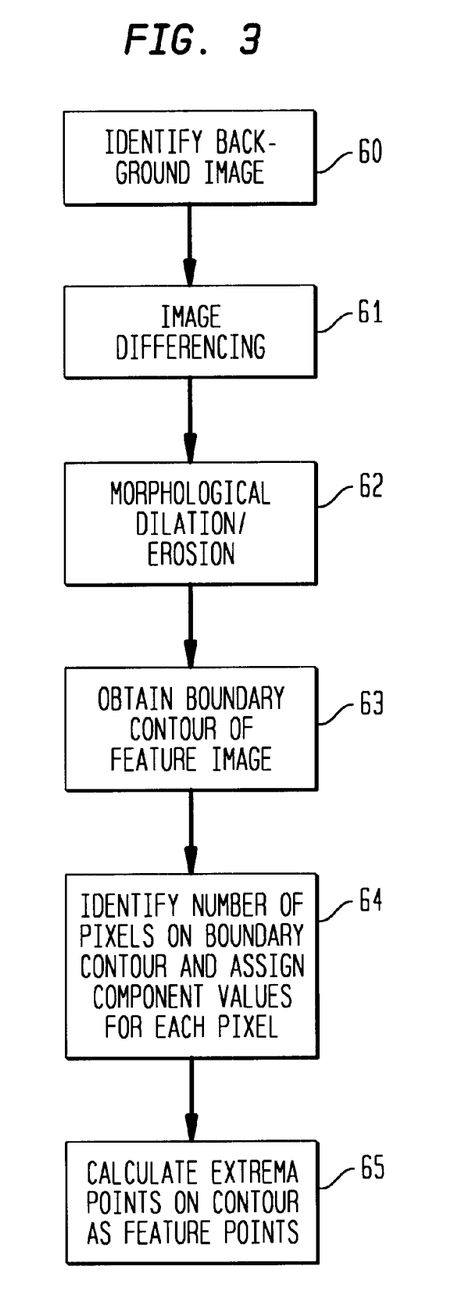
FIG. 3 is a flow chart illustrating examples of motion region extraction and feature extraction (steps 34 and 36) of the method shown in FIG. 1.

With reference now to FIG. 3, an example of a method for detecting feature points on the contours of images will now be described. To locate an object image, i.e. an image of a person, from within a current frame, the object image must be separated from a background image. Thus, the generally static background image must initially be identified and defined. One way of accomplishing this is to examine a large number of frames of a scene taken by the camera 12 and to obtain the mean value of all color components at each pixel over all of the frames. The standard deviation of each color component is also computed for each pixel over all of the frames and the mean value for the standard deviation is computed over all pixels. The mean value of each pixel is then subtracted from corresponding pixels in the current frame and the resulting values are thresholded, as mentioned above, to further distinguish objects in the current frame from the background. This results is an image of objects that were not in the static scene, i.e., the scene formed of the initial frames used to compute the background image. When camera 12 is positioned in a location at which the moving objects are primarily people, the resulting highlighted regions thus correspond to people or parts of people. It should be understood that this technique for obtaining an object image is but one of several such techniques which are known in the art; accordingly, it is emphasized that other known techniques may be also employed within the intended scope of the present invention.

The above-described method of obtaining an object image and separating it from a background image (i.e., the step 30 of image differencing) is represented by steps 60 and 61 of FIG. 3. Once an object is identified, a contour or boundary of the object image is obtained using a standard contour tracing algorithm such as, for example, the algorithm described in Pavlidis, T., Structural Pattern Recognition, Springer Verlag, N.Y., 1977. From these bounding contours, a complete contour of the object is obtained. A structure corresponding to each contour is defined and each structure contains coordinates including position coordinates (x,y coordinates), orientation, curvature and color component values for every pixel on the contour. The structure also contains the size of the particular contour (i.e. the total number of pixels on the contour). The orientation and curvature components of each contour are computed by first passing each x and y coordinate value through a circular average filter, as in known by those of ordinary skill in the art. The orientation for each point on each contour is computed as the orientation of a chord connecting the end points of a window centered on a particular point-of-interest on the contour. The curvature is computed as the difference in orientations of the end points of a window centered on the point of interest. For the curvature computation, the window size is chosen as typically half of the window size for the orientation computation. These features of the method are set forth in steps 62 and 63 of FIG. 3.

Each contour is preferably uniformly closed or completed by, for example, the morphological dilation/erosion process discussed hereinabove and indicated in FIG. 3 as step 64.

Each object corresponding to each contour has particular features associated therewith and corresponding to, for example, the arms, legs and head of the person(s) represented by the contours. These features are located by calculating the extrema points on the contour. The points are then located by processing each curvature value with a circular average filter, as is generally known in the art. The extrema points on the contour are found as the values at which the zero crossings of the derivative of the curvature are located; upon location of the extrema points, all of the identifying features or components of each contour are stored in a memory. Typical contour components include x, y coordinates, orientation, curvature, color component values and an index identifying the location of each feature point on the contour. The identification of the feature points is performed by step 65 of FIG. 3.

Figure 4:
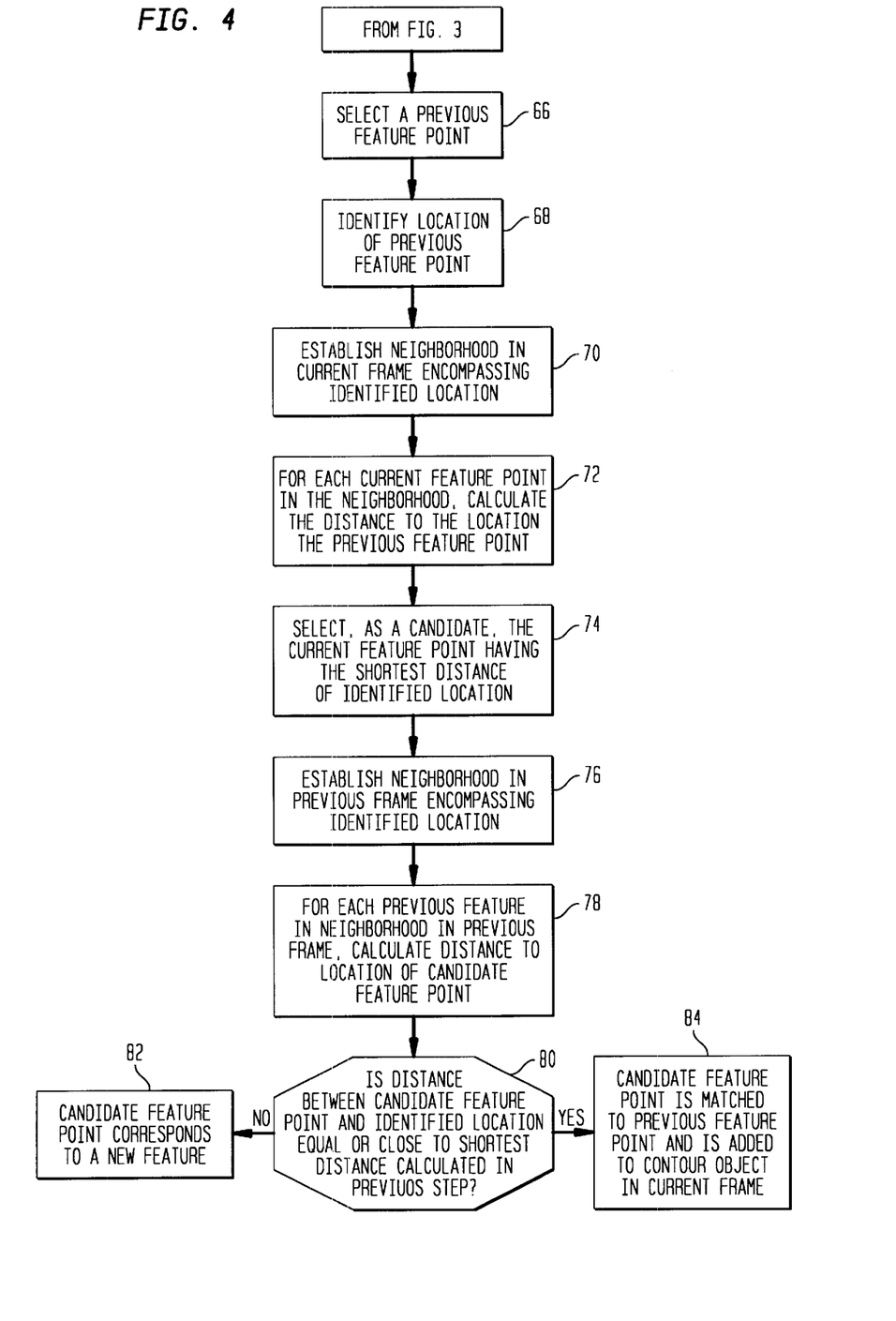
FIG. 4 is a flow chart illustrating an example of feature matching (step 38) of the method shown in FIG. 1.

To track moving people, such as athletes, in real time according to the present invention, the identified feature points of the current frame must be correlated or otherwise associated with existing or previous feature points identified by the above-described process in previous frames. A preferred method of coordinating existing feature points with prior feature points is illustrated in FIG. 4. Initially, a previous feature point is selected from a contour identified in the immediately preceding video frame and the location of the selected previous feature point is identified (steps 66 and 68). With the location of the previous feature point known, a neighborhood or boundary is established in the current frame encompassing the identified location (step 70). The neighborhood established in the current frame will typically encompass several current feature points. For each current feature point contained in the neighborhood, the distance between each current feature point and the selected previous feature point is calculated according to the following equation:

$$(dx^2+dy^2)/\sigma_x^2+do^2/\sigma_o^2+dc^2/\sigma_c^2 \qquad (1)$$

where dx, dy, do and dc, respectively, correspond to the difference in the location (x,y), the orientation, and the curvature values between the feature point and the current point. The distance calculation is not an Euclidean calculation but is computed on a weighted formula with the lowest weight associated with the x and y components. Typical weights for the components are:

$\sigma_x=3$, $\sigma_o=10$ and $\sigma_c=10$.

Once the distances between a selected previous feature point and each current feature point in the neighborhood have been calculated (step 72), the current feature point within the neighborhood corresponding to the shortest calculated distance is selected as a candidate for the new feature point corresponding to the selected previous feature point (step 74), i.e., a candidate for a match. Although this method of selecting a current feature point from the location of a selected previous feature point may be sufficiently accurate for some applications, in this embodiment it is preferable that the candidate match point be used as a reference check to insure that the candidate current feature point is in fact the correct match for the selected previous feature point.

This is accomplished by establishing a neighborhood in the immediately preceding frame, i.e., the frame containing the previously selected feature point, about the location of the chosen candidate match point. The neighborhood will contain other previously identified feature points as well as the previously selected feature point. The distance is again calculated using equation (1) between the candidate match point and each of the previous feature points in the neighborhood. The candidate point chosen in step 74 is the correctly identified corresponding point to the previously selected feature point in step 66, i.e., the correct match, if the distance between the candidate feature point and the identified location of the previous feature point equals or is within a minimum range to the shortest distance calculated between each previous feature point in the neighborhood and the location of the candidate feature point (step 84). If the candidate feature point is not within a certain minimum threshold distance to the previous feature point location, then the candidate feature point is identified as a new feature point and is added as a new point on the contour of the object in the current frame (step 82). This decision process takes place in step 80.

It should be understood that the movement of the feature points from one frame to the next indicates motion of the corresponding feature across the frames of the video signal. This motion is represented in terms of feature paths that are formed out of current and corresponding previous feature point pairs. The structure of each feature path contains x, y position coordinates as well as time coordinates for each feature point along each path. In addition, each feature path is indexed to a particular contour object and each feature path structure has a starting time at which the particular path began, the length of the path, a bounding spatial rectangle containing the path, and status bits to indicate whether the path structure is associated with a current (i.e., currently active) cluster, as more fully explained below, or if the path has ended. The path structure contains x, y and time coordinates for each feature point along the path as well as an index to the contour object for each point. In addition, the path structure denotes the creation time of the path and includes status bits to indicate whether the path structure is free and if the path has ended. A path at time t may be represented by $P(k,t)$, where k is an index to a path which varies from 1 to $p_t$ and $p_t$ is the total number of valid paths at time t. P has components $(l, cx, cy, x_1, y_1, t_1, x_2, y_2, t_2, \ldots x_1, y_1, t_1)$ where l is the length of the path and $(x_i, y_i, t_i)$ are the spatio-temporal coordinates of each point on the path. The terms (cx, cy) indicate the mean displacement of the path from its associated cluster, as is more fully described below.

When a feature point in an immediately preceding frame is matched, as explained above, to a feature point in the current frame, the feature path corresponding to the previous feature point is associated with the current feature point and that path is extended and updated to include the current feature point. In other words, the coordinates of the current feature point are included in the previous path coordinates and the values for the path length, bounding rectangle, etc. are also updated. For each feature point in the immediately preceding frame that does not find a match to a feature point in the current frame, the feature path associated with the previous point is ended by switching off the status bit for that path. On the other hand, for each feature point in the current frame with no match to a feature point in the previous frame, a new path of unity length is created containing only the parameters of the current feature point.

The existing feature paths indicate the motion of a particular feature, such as an arm or leg of an athlete, from one frame to the next. Thus, each athlete's image in each frame will have a plurality of feature paths associated with it, i.e. separate paths for the person's body and extremities, respectively. The plurality of paths corresponding to a single person are each typically short in duration and partially overlap in time. To track the motion of a person in the scene, the paths associated with the particular person must be grouped together to form a cluster of paths. In other words, each path corresponding to feature movement is associated with a cluster corresponding to movement of that person. Accordingly, it should be understood that a cluster will have a structure similar to the structure of a feature path, i.e., will include x, y and time coordinates for each point along the cluster. In addition, each point comprising a cluster has an indicator signifying the total number of paths contributing to that particular cluster point. The mean and variance of the x and y coordinates across all points comprising each cluster as well as the total number of points contributing to the cluster are also maintained. Lastly, each cluster has a particular length associated therewith.

A path cluster at time t may be represented by $z(k,t)$ where k is an index to the cluster and varies from 1 to $Z_t$, and where $Z_t$ is the total number of valid clusters at time t. A cluster Z has components $(l, bx, by, bxx, byy, bk, x_1, y_1, t_1, n_1, x_2, y_2, t_2, n_2, \ldots, x_i, y_i, t_i, n_i)$ where l is the length of the cluster, $(x_i, y_i, t_i)$ represent the spatio-temporal coordinates of each point on the cluster, and n, represents the number of feature points contributing to the ith cluster point. The terms (bx, by) indicate the mean displacement of the position of a path contributing to the cluster from the coordinates $(x_i, y_i)$ of the cluster. The terms (bxx, byy) indicate the variances in the displacement of the position of a path contributing to the cluster from the cluster coordinates. The term "bk" represents the total number of paths contributing to the cluster.

As noted above, the method according to the present invention attempts to associate each existing feature path with an existing cluster formed from previous frames. If a particular feature path cannot be associated with an existing cluster, then a new cluster encompassing that feature path is formed.

Figure 5:
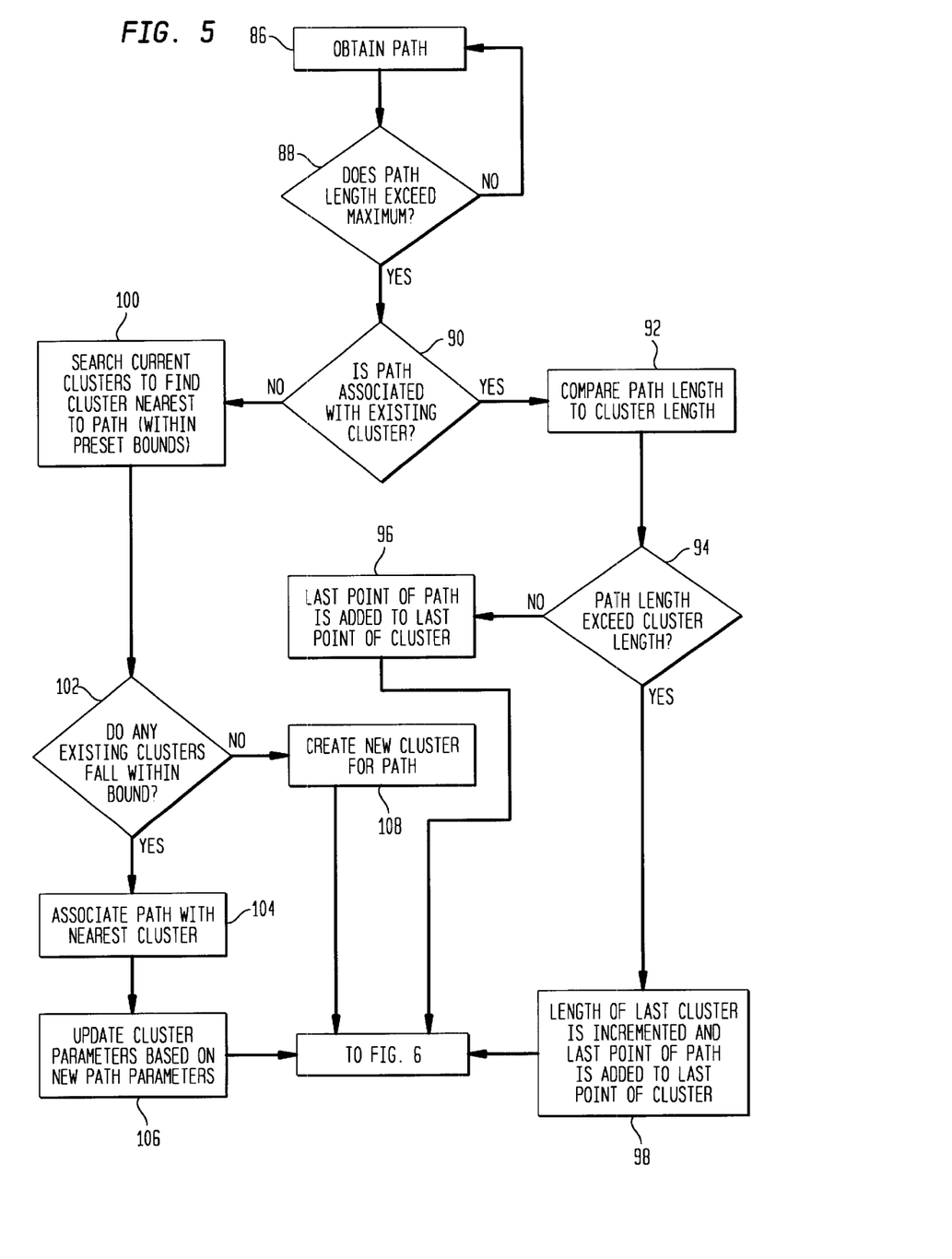
FIG. 5 is a flow chart illustrating examples of updating feature paths and updating path clusters (steps 40 and 42) of the method shown in FIG. 2.

The inventive method for determining an appropriate existing cluster for association with each existing current feature path is depicted in FIG. 5 and will now be described.

Once a feature path is selected from the current frame (step 86), the length of that path is measured to determine whether the path exceeds a certain predetermined minimum length (step 88). If it does not, then a different current path is obtained and its length is measured against the minimum length. If that path length does exceed the minimum, then a determination is made as to whether that path is already associated with an existing cluster (step 90). In other words, a determination is made as to whether the current path is representative of movement of a feature which is already associated with an existing cluster established from previous frames of the video signal; if so, the associated cluster is updated utilizing the parameters of the current path. For example, the overlap between the path and the cluster is checked to determine whether the length of the cluster requires adjustment, as by extending the cluster length (steps 92 and 94). If the length of the cluster must be extended, the length of the cluster is incremented and the last point of the path becomes the last point of the cluster (step 98). If, however, it is determined that the cluster length need not be extended, then the parameters or components of the last point of the path is used to update the last point of the cluster, i.e., the position, color, curvature, etc. (step 96).

For example, if a path P of length p has an associated cluster Z of length q, then the cluster update proceeds as follows. If $P_{t_p} = Z_{t_q}$ the cluster is updated as $$(Z'_{x_q}, Z'_{y_q}) = \left( \frac{Z_{x_q} Z_{n_q} + P_{x_p} - P_{cx}}{Z_{n_q} + 1}, \frac{Z_{x_q} Z_{n_q} + P_{x_p} - P_{cy}}{X_{n_q} + 1} \right) \quad (3)$$

$$Z'_{n_q} = Z_{n_q} + 1 \quad (4)$$

where $Z_{x_q}$, $Z_{y_q}$ and $Z_{n_q}$ represents the updated cluster parameter values. $P_{cx}$, and $P_{cy}$ are calculated when the path is first associated with the cluster, as is more fully described below.

If $P_{t_p} \neq Z_{t_q}$ then the cluster is updated as follows:

$$q' = q + 1 \quad (5)$$

$$Z_{x_{q'}} = P_{x_p} - P_{cx} \quad (6)$$

$$Z_{y_{q'}} = P_{y_p} - P_{cy} \quad (7)$$

$$n_{q'} = 1 \quad (8)$$

As seen in the foregoing relationships, the cluster update involves the computation of new mean values for the x and y coordinates of the cluster based on the current path and the existing means and "count" values.

If, on the other hand, a current path has a length exceeding a minimum and is not yet associated with an existing cluster, i.e., the feature corresponding to the path has not yet been grouped with or represented by an existing cluster, then the existing clusters are searched to find a candidate cluster or "match" with the subject path. The cluster having the shortest distance to the path will of course be selected as the candidate. To determine this, the overlap lengths of the selected or current path with any existing clusters are computed. The sum of the mean squared difference between the x and y values of the path and the cluster is then computed over their entire overlap length. This measurement is a first distance measurement which is designated as "d" and is computed as follows:

$$d = \frac{1}{l} \left( \sum_{i=0}^{l-1} (P_{x_{a+i}} - Z_{x_{r+i}})^2 \right) + \frac{1}{l} \left( \sum_{i=0}^{l-1} (P_{y_{a+i}} - Z_{y_{r+i}})^2 \right) \quad (9)$$

where $P_{t_a} = Z_{t_r}$ represents the first instant of overlap between the path and the cluster. Another distance $\Delta$ is computed as the normalized sum of the mean squared distances of the x and y components of the tangent vectors along the path and the cluster over their overlap length. This distance $\Delta$ is computed as follows:

$$\Delta = \frac{\sum_{i=0}^{l-1} \left[ (P_{\tau x_{a+i}} - Z_{\tau x_{r+i}})^2 + (P_{\tau y_{r+i}} - Z_{\tau y_{r+i}})^2 \right]}{\text{Min} \left( \sum_{i=0}^{l-1} (P^2_{\tau x_{a+1}} + P^2_{\tau y_{a+i}}), \sum_{i=o}^{l-1} (Z^2_{\tau x_{r+i}} + Z^2_{\tau y_{r+i}}) \right) + 2l} \quad (10)$$

Thus, $\Delta$ is normalized for the values of the tangential components (velocity vectors) and for the overlap length. The tangent at each point along the path or cluster is estimated as a difference between the outputs of two linear predictive filters applied to the x and y components of the path or cluster trajectory in opposition directions, as shown below for the x a component of a path:

$$P_{\tau x_i} = P_\tau 1_{x_i} - P_\tau 2_{x_i}, \ i = 1, 2, \ldots p \quad (11)$$

where p is the length of the path and $$P_\tau 1_{x_i} = P_\tau 1_{x_{i+1}} + \alpha (P_{x_i} - P_\tau 1_{x_{i+1}}) \quad (12)$$

$$P_\tau 1_{x_p} = P_{x_p} \quad (13)$$

and $$P_\tau 2_{x_i} = P_\tau 2_{i-1} + \alpha (P_{zx_i} - P_\tau 2_{x_{i-1}}), \quad (14)$$

$$P_\tau 2_{x_1} = P_{x_1} \quad (15)$$

If the distances "d" and "$\Delta$" lie within certain preset bounds, then the final distance between the path and the path and a cluster is computed using the following equation:

$$D = \frac{\text{Max}(xx, xd)}{\rho_x^2} + \frac{\text{Max}(yy, yd)}{\rho_y^2} + \frac{\Delta}{\rho_\tau^2} \quad (16)$$

where $p_x$, $p_y$ and $p_t$ are weighing factors for the x, y and tangential distances, i.e. distances between velocity vectors. $p_x$ and $p_y$ are chosen based on typical dimensions of a person in the image. Typical values are $p_x = 45$, $p_y = 75$ and $p_t = 0.9$.

The xx, yy, xd and yd components are calculated as follows:

$$\beta_x = \frac{1}{l}\sum_{i=0}^{l-1}(P_{x_{a+i}} - Z_{x_{r+i}}) \qquad (17)$$

$$\beta_y = \frac{1}{l}\sum_{i=0}^{l-1}(P_{y_{a+i}} - Z_{y_{r+i}}) \qquad (18)$$

$$xd=(\beta_x-Z_{bx})^2 \qquad (19)$$

$$yd=(\beta_y-Z_{by})^2 \qquad (20)$$

$$\gamma_x = \frac{Z_{bx}Z_{bk} + \beta_x}{Z_{bk} + 1} \qquad (21)$$

$$\gamma_y = \frac{Z_{by}Z_{bk} + \beta_y}{Z_{bk} + 1} \qquad (22)$$

$$xx = \frac{((Z_{bx}-\gamma_x)^2 + Z_{bxx})Z_{bk} + (\beta_x - \gamma_x)^2}{Z_{bk} + 1} \qquad (23)$$

$$yy = \frac{((Z_{by}-\gamma_y)^2 + Z_{bxx})Z_{bk} + (\beta_y - \gamma_y)^2}{Z_{bk} + 1} \qquad (24)$$

In the foregoing equations, $(\beta_x, \beta_y)$ provide the mean displacement or translation of the path P from the cluster Z over their overlap length, and $(x_d, y_d)$ the square of the difference between the existing mean value $(Z_{bx}, Z_{by})$ and the mean displacement $(\beta_x, \beta_y)$ for displacement of paths contributing to the cluster Z. In addition, $(\gamma_x, \gamma_y)$ represent the new mean values for path displacement from the cluster if P is merged with Z, and (xx,yy) represent the new variance in path displacements from the cluster if P is merged with Z.

Thus, D measures the displacement of the path from the cluster, i.e. the spread of the paths contributing to the cluster, and weighs these calculations with respect to the typical dimensions of a person. The cluster with the smallest value for the distance D from the path (assuming that the distance D is within a preset bound) is selected as the nearest cluster to the path whereupon the path is associated with the selected cluster (steps 100, 102, and 104).

Once the path is assigned, the cluster parameters are updated, based on the parameters of the newly-included path over the overlap length, according to the following equations in which i varies from 0 to l-1 (step 106):

$$P_{cx} = \frac{1}{l}\sum_{i=0}^{l-1}(P_{x_{a+i}} - Z_{x_{r+i}}) \qquad (25)$$

$$P_{cy} = \frac{1}{l}\sum_{i=0}^{l-1}(P_{x_{a+i}} - Z_{x_{r+i}}) \qquad (26)$$

$$(Z'_{x_{r+i}}, Z'_{y_{r+i}}) = \frac{Z_{x_{r+i}}Z_{n_{r+i}} + P_{x_{a+i}} - P_{cx}}{Z_{n_{r+i}} + 1}, \frac{Z_{y_{r+i}}Z_{n_{r+i}} + P_{y_{a+i}} - P_{cy}}{Z_{n_{r+i}} + 1} \qquad (27)$$

$$Z'_{n_{r+i}} = Z_{n_{r+i}} + 1 \qquad (28)$$

$$Z'_{bx} = \frac{Z_{bx}Z_{bk} + P_{cx}}{Z_{bk} + 1} \qquad (29)$$

$$Z'_{by} = \frac{Z_{bx}Z_{bk} + P_{cy}}{Z_{bk} + 1} \qquad (30)$$

$$Z'_{bxx} = \frac{(Z_{bxx} + Z_{bx}^2)Z_{bk} + \beta_x^2}{Z_{bk} + 1} - (Z'_{bx})^2 \qquad (31)$$

$$Z'_{byy} = \frac{(Z_{byy} + Z_{by}^2)Z_{bk} + \beta_y^2}{Z_{bk} + 1} - (Z'_{by})^2 \qquad (32)$$

If the path length p is greater than the overlap length l of the path and the cluster, the cluster is extended as follows, with i varying from 1 to p−1, $$(Z_{x_{r+i}}, Z_{y_{r+i}}) = (P_{x_{a+i}} - P_{cx}, P_{y_{a+i}} - P_{cy}) \qquad (33)$$

$$Z_{n_{r+i}} = 1 \qquad (34)$$

If, however, the distance D falls outside of a preselected boundary, then the path cannot be associated with any existing cluster, whereupon a new cluster is created for that path (step 108).

When all current paths from a current frame have either been associated with an existing cluster or incorporated in a newly-formed cluster, the remaining clusters are then checked to determine whether any of them can be merged with another. Thus, if two or more clusters represent movement of the same object or person, these clusters will be merged into a single cluster; this technique is similar to that described with respect to FIG. 5 for incorporating existing paths with existing clusters. Specifically, all of the remaining clusters are searched to locate the nearest cluster. If two clusters are within a certain minimum distance from each other, then those clusters are merged. This process is repeated until no additional mergers are possible, i.e., until the distance between respective clusters exceeds the minimum "merging" distance threshold. The distance between two respective clusters is calculated in a similar manner to that set forth above. In the following equations, P refers to the selected cluster for which possible mergers are being sought, and Z refers to a candidate cluster for merger with the selected cluster P. Thus, equations 17–22 are modified for these calculations as follows:

$$xd=(P_{bx}+\beta_x-Z_{bx})^2 \qquad (35)$$

$$yd=(P_{by}+\beta_y-Z_{by})^2 \qquad (36)$$

$$\gamma x = \frac{Z_{bx}Z_{bk} + (P_{bx} + \beta_x)P_{bk}}{Z_{bk} + P_{bk}} \qquad (37)$$

$$\gamma y = \frac{Z_{by}Z_{bk} + (P_{by} + \beta_y)P_{bk}}{Z_{bk} + P_{bk}} \qquad (38)$$

$$xx = \frac{((Z_{bx}-\gamma_x)^2 + Z_{bxx})Z_{bk} + ((P_{bx}+\beta_x-\gamma_x)^2 + P_{bxx})P_{bk}}{Z_{bk} + P_{bk}} \qquad (39)$$

$$yy = \frac{((Z_{by}-\gamma_y)^2 + Z_{byy})Z_{bk} + ((P_{by}+\beta_y-\gamma_y)^2 + P_{byy})P_{bk}}{Z_{bk} + P_{bk}} \qquad (40)$$

Figure 6:
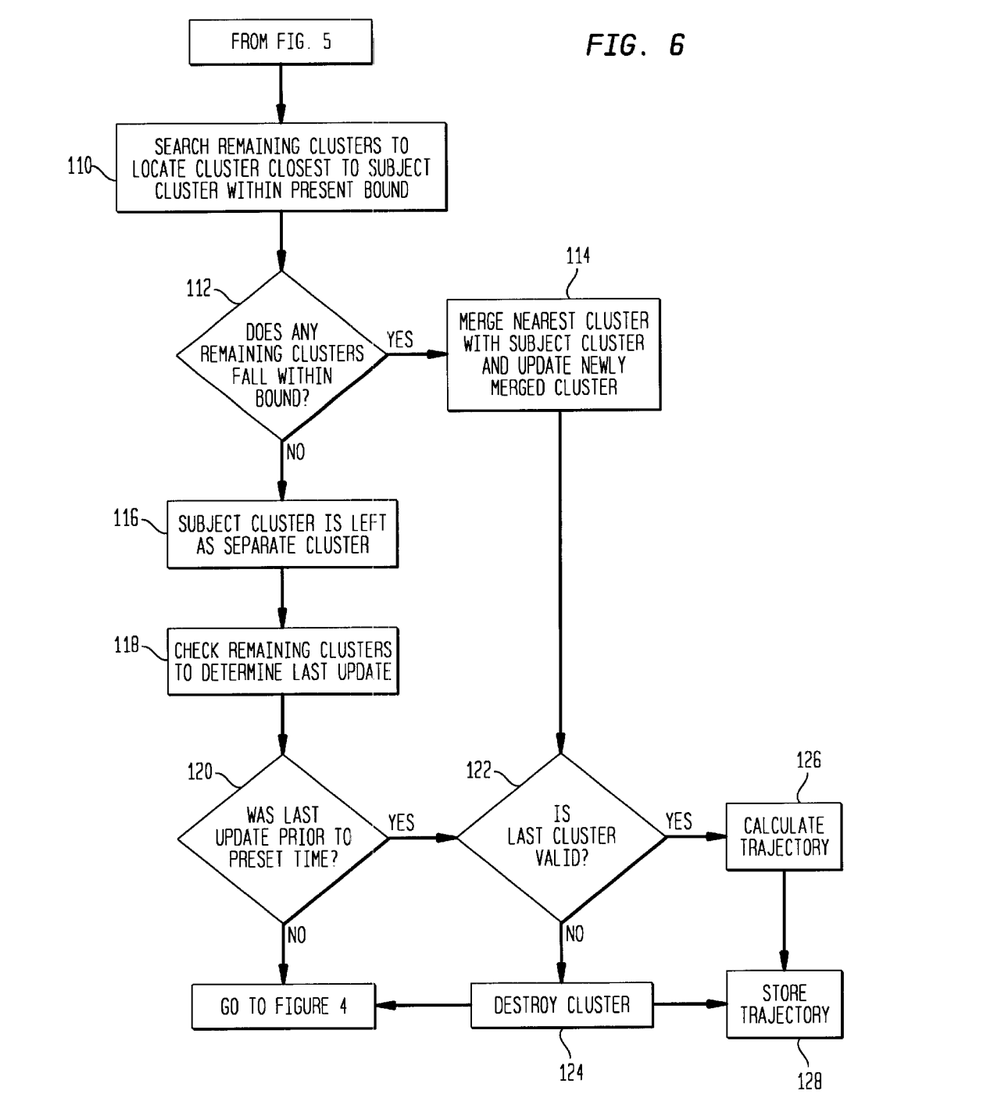
FIG. 6 is a flow chart illustrating an example of identifying completed trajectories (step 44) of the method shown in FIG. 2.

Again, the candidate cluster Z having the smallest distance "D" within a preset "merging" distance from the selected cluster P is chosen for merging with cluster P. After merger, the resulting combined cluster is updated (steps 110, 112, and 114). If the length of the selected cluster P is less than the end point of the candidate cluster Z, then the updated values of the merged cluster over the overlap length between the candidate and selected clusters are obtained using the following equations:

$$(Z'_{x_{r+i}}, Z'_{y_{r+i}}) = \frac{Z_{x_{r+i}}Z_{n_{r+i}} + (P_{x_{a+i}} - \beta_x)P_{n_{a+i}}}{Z_{n_{r+i}} + P_{n_{a+i}}}, \quad (40)$$

$$\frac{Z_{y_{r+i}}Z_{n_{r+i}} + (P_{y_{a+i}} - \beta_y)P_{n_{a+i}}}{Z_{n_{r+i}} + P_{n_{a+i}}}$$

$$Z_{n_{r+i}} = Z_{n_{r+i}} + P_{n_{a+i}} \quad (42)$$

$$Z'_{bx} = \frac{Z_{bx}Z_{bk} + (P_{bx} + \beta_x)P_{bk}}{Z_{bk} + P_{bk}} \quad (43)$$

$$Z'_{by} = \frac{Z_{by}Z_{bk} + (P_{by} + \beta_y)P_{bk}}{Z_{bk} + P_{bk}} \quad (44)$$

$$Z'_{bxx} = \frac{Z_{bxx} + (Z_{bx} - Z'_{bx})^2 Z_{bk} + (P_{bxx} + (P_{bx} + \beta_x - Z'_{bx})^2) P_{bk}}{Z_{bk} + P_{bk}} \quad (45)$$

$$Z'_{byy} = \frac{Z_{byy} + (Z_{by} - Z'_{bx})^2 Z_{bk} + (P_{byy} + (P_{by} + \beta_y - Z'_{by})^2) P_{bk}}{Z_{bk} + P_{bk}} \quad (46)$$

If, however, the length of the selected cluster P extends beyond the end point of the candidate cluster Z, then the candidate cluster Z is extended as follows (with i varying from 1 to p–1):

$$(Z_{x_{r+i}}, Z_{y_{r+i}}) = (P_{x_{a+i}} - \beta_x, P_{y_{a+i}} - \beta_y) \quad (47)$$

$$Z_{n_{r+i}} = P_{n_{a+i}} \quad (48)$$

If the smallest distance "D" between the selected cluster P and any of the current clusters is greater than the minimal "merging" distance, then the subject cluster P is treated as a separate cluster and is not merged (step 116).

The above-described technique permits the grouping of cluster evidence which is gathered over a plurality of frames from a video signal while operating in real time. The grouping or merging is formed not only for the clusters in the current frame but for clusters from previous frames as well. Thus, estimates of the position of a person in a particular frame are continually refined and updated on the basis of data or evidence obtained in subsequent frames.

Once all mergers have taken place, as explained above, the existing clusters are examined to determine when the respective last update of each occurred (step 118). If a cluster has not been updated within a predetermined length of time (step 120), it is likely that the person associated with that cluster has moved out of view of the camera and, thus, that the cluster associated therewith can now be destroyed (step 124). Before doing so, however, it is preferable that the cluster be first checked to determine if it is valid (step 122), i.e., if the cluster length is greater than a minimum length and the cluster has a minimum number of feature points contributing thereto. If this is the case, then the trajectory or track corresponding to each valid cluster (step 126) may be stored in memory 16 (see FIG. 7) (step 128) and used to derive performance statistics for the athlete(s) being tracked.

It should be further understood that various techniques may be used to calculate feature points on the contours of objects and that the particular technique described herein for that purpose is simply the presently preferred technique. In addition, it is noted that for some systems, all points on an image and not just the contour points can be used to obtain motion paths for grouping into clusters.

In another embodiment of the present invention, instead of obtaining performance statistics based on the sporting event being tracked, a visual occupancy map illustrating an athlete's "coverage" of a playing area is obtained.

Figure 8:
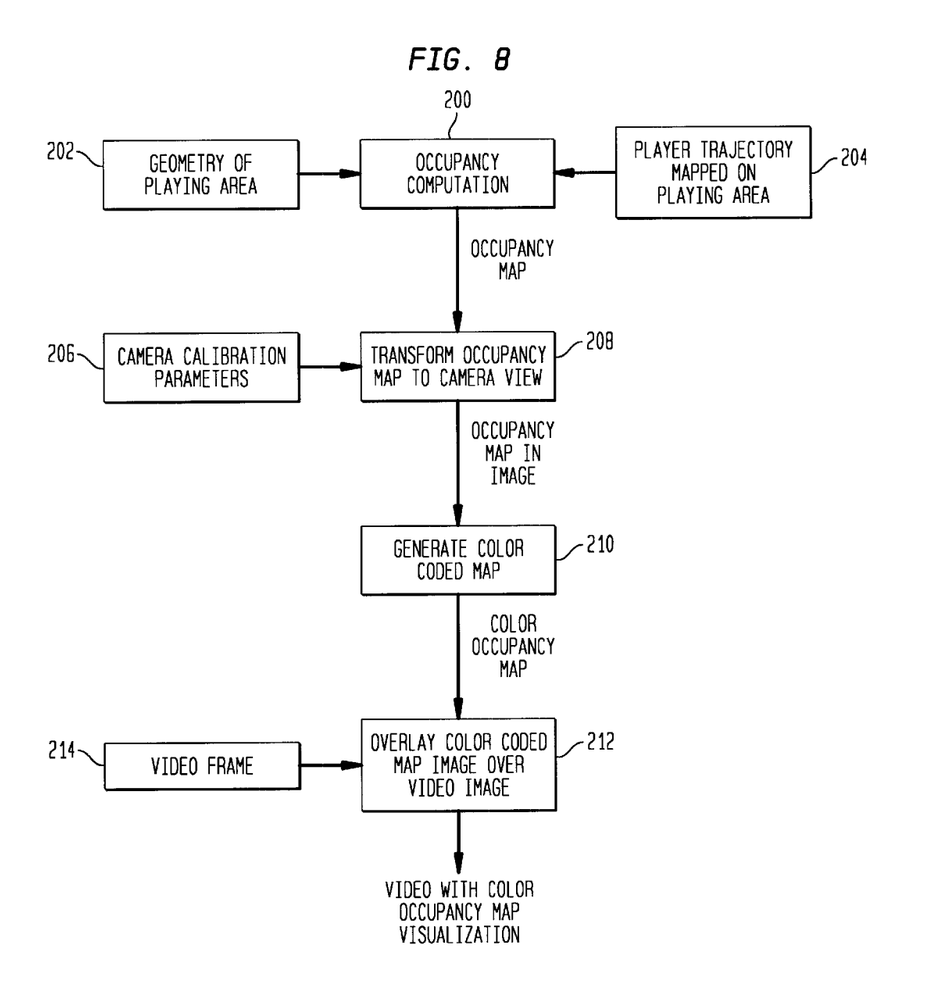
FIG. 8 is a flow chart illustrating an example embodiment according to the present invention wherein an occupancy map showing an athlete's coverage of a playing area is obtained.

FIG. 8 is a flow chart illustrating the steps involved in obtaining such an occupancy map. FIG. 8 starts at a point between steps 48 and 50 as shown in FIG. 3. The steps disclosed hereinabove with regard to the apparatus and method for real time tracking, in general, are highly applicable to this embodiment, although other methods may be usable as well.

In FIG. 8, the geometry of the playing area 202 and an athlete trajectory 204 mapped onto the playing area are input in step 200 in order to calculate the athlete's occupancy of the playing area. For example, the playing area is subdivided into a plurality of zones. For each zone, the time spent by the athlete in that zone, or the number of times the athlete traveled to that zone is calculated over time based on the athlete's path of travel (as embodied by the previously derived trajectory) relative to the plurality of zones. The output of step 200 is an occupancy map describing which zones were occupied or otherwise traversed by the athlete and the time spent in each respective zone. Then in step 208, the occupancy map is mapped to the view of a given camera, using the calibration parameters 206 of that camera, so that the occupancy map can be realized visually relative to the actually playing area. This is, of course, similar to step 48 in FIG. 2, whereby the athlete trajectory was mapped to the image plane of a camera.

In step 210, the occupancy map is preferably "colorized" in a conventional fashion whereby respective zones are given, for example, a representative color indicating, for example, the number of times those zones were occupied and/or traversed by the athlete, or the comparative amount of time spent in each zone. This gives the colored occupancy map almost the effect of a statistical histogram, whereby such accumulated information such as occupation frequency and the like is made easily understandable. It will be obvious that the present invention in this regard also includes other forms of visual "coding," such as using different levels of gray shading, cross-hatching, or the like, instead of different colors.

Finally, in step 212, using a video image 214 as an input, the color occupancy map is overlaid on the regular video image, whereby the color occupancy map is viewable directly in the context of the playing area in question.

In yet another embodiment of the present invention, the tracking information obtained from real time tracking of a sporting event is used to generate a computerized replay of the athletic play.

Figure 9:
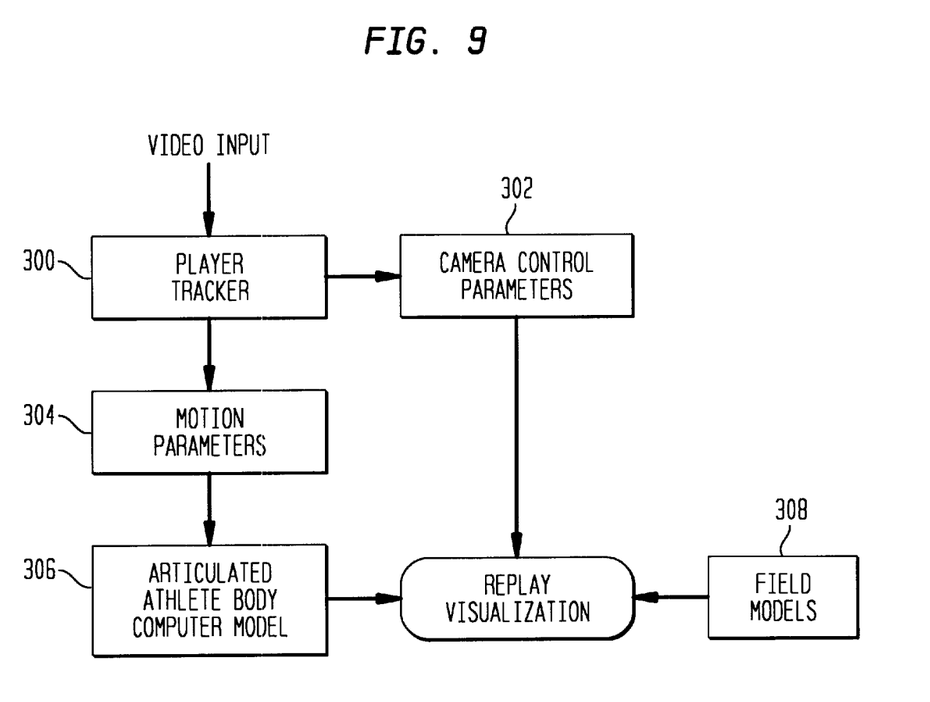
FIG. 9 is a flow chart illustrating an example embodiment according to the present invention wherein a computerized replay is obtained based on the trajectories derived from real time tracking of athletes.

FIG. 9 illustrates a system for generating such a computerized replay.

The output of box 300 (labelled "player tracker") is a trajectory corresponding to the movement of an athlete on the playing field, and is generally equivalent to, for example, the output after step 44 in FIG. 2.

The athlete trajectory information from player tracker 300 is translated into motion parameters 304 for controlling and driving an articulated computer animated athlete model 306 and, secondarily, is translated into camera control parameters 302 for controlling one or more virtual cameras through which the computerized replay is viewed. In particular, the camera control parameters take into account the orientation of the virtual camera(s) relative to the Avatar.

Accordingly, the motion parameters 304 are duly provided to the athlete model 306 whereby the model 306 emulates the motion of the real athlete.

The last input to the replay visualization (in addition to the appropriately driven athlete model and the control parameters for the virtual camera(s)) is computer rendition of the playing field (308) so as to provide a visual context for the replay.

It will be appreciated that the current state of computer animation is quite developed, and that any conventionally known method for enabling the computer animated athlete model as well as computerized rending of the playing field would be appropriate to the present invention.

Thus, while there have been shown and described and pointed out fundamental novel features on the invention as applied to preferred embodiments thereof, it will be understood that various omissions and substitutions and changes in the form and details of the devices illustrated, and in their operation, and in the method illustrated and described, may be made by those skilled in the art without departing from the spirit of the invention. For example, it is expressly intended that all combinations of those elements and/or methods steps which perform substantially the same function in substantially the same way to achieve the same results are within the scope of the invention. It is the invention, therefore, to be limited only as indicated by the scope of the claims appended hereto.

What is claimed is:

1. A method for deriving information related to athletes participating in a sporting event from real time tracking of the sporting event, comprising the steps of:
   determining a spatio-temporal trajectory corresponding to motion of an athlete participating in the sporting event;
   analyzing the trajectory with respect to time to extrapolate information corresponding to the motion; and
   outputting the extrapolated information.

2. The method according to claim 1, wherein said information is any one of instantaneous speed, average speed, instantaneous acceleration, peak speed, distance travelled, locations travelled to, frequency of occupation of a particular region, and time spent in a particular region.

3. The method according to claim 1, wherein said outputting step comprises outputting the extrapolated information to a searchable database.

4. The method according to claim 1, wherein said outputting step comprises outputting the extrapolated information to a video broadcast as part of an on-screen text display.

5. The method according to claim 1, wherein said determining step comprises the steps of:
   obtaining a real time video image of the sporting event, the video image including a current frame and previous frames;
   identifying a region of motion in the video image corresponding to motion of an athlete participating in the sporting event;
   identifying a local feature of the region of motion;
   matching the local feature in the current frame with a corresponding local feature in a previous frame to define a feature path; and
   matching the feature path with a cluster of feature paths selected from among a plurality of clusters of feature paths, the plurality of clusters collectively representing the motion of the athlete, wherein a candidate cluster for matching with said feature path is closest in distance to the feature path.

6. The method of claim 5, further comprising the step of updating the cluster matched with the feature path in accordance with the characteristics of the feature path.

7. The method of claim 5, wherein said determining step comprises coupling the trajectory with positioning parameters from a video camera by which the real time video image is obtained and mapping the trajectory onto a playing area where the sporting event is taking place, from the perspective of the video camera.

8. The method according to claim 5, comprising the step of deciding whether a cluster is active or inactive, and, if inactive, destroying that cluster.

9. An apparatus for deriving information related to athletes participating in a sporting event from real time tracking of the sporting event, comprising:
   a device for obtaining a spatio-temporal trajectory based on the tracking of the motion of an athlete participating in the sporting event;
   a computational device constructed and arranged to extrapolate information corresponding to the motion based on said trajectory over time; and
   a statistical device constructed and arranged to compile said performance information.

10. The apparatus of claim 9, comprising a database device constructed and arranged to store said compiled performance information for retrieval in response to a query posed thereto.

11. The apparatus of claim 9, comprising a data storage device constructed and arranged to store said compiled performance information.

12. The apparatus of claim 9, comprising a video output device constructed and arranged to convert said compiled performance information into graphical form for on-screen display.

13. The apparatus of claim 9, wherein the extrapolated information is any one of instantaneous speed, average speed, instantaneous acceleration, peak speed, distance travelled, locations travelled to, frequency of occupation of a particular region, and time spent in a particular region.

14. The apparatus of claim 9, further comprising a frame grabber/digitizer for obtaining a single frame from said video signal and for digitizing said single frame and passing said digitized single frame to said CPU.

15. The apparatus of claim 14, further comprising a host memory provided between said frame grabber/digitizer and a CPU for storing said single digitized frame.

16. The method according to claim 1, wherein the step of determining said spatio-temporal trajectory obtains motion data from said athlete passively.

17. The apparatus of claim 9, wherein said device for obtaining said spatio-temporal trajectory is operable to obtain motion data from said athlete passively.

18. The method according to claim 1, wherein the step of determining said spatio-temporal trajectory selectively clusters points on a contour corresponding to at least a part of said athlete in order to determine said trajectory.

19. The apparatus of claim 9, wherein said device for obtaining said spatio-temporal trajectory is operable to selectively cluster points on a contour corresponding to at least a part of said athlete in order to determine said trajectory.

* * * * *